(12) United States Patent
Watkins et al.

(10) Patent No.: US 10,278,867 B2
(45) Date of Patent: May 7, 2019

(54) HELMET ASSEMBLIES WITH FLIP-TYPE WELDING VISORS

(71) Applicant: A.C.E. International, Taunton, MA (US)

(72) Inventors: James Watkins, East Taunton, MA (US); Ed Martin, Plymouth, MA (US)

(73) Assignee: A.C.E. INTERNATIONAL, Taunton, LA (US)

( * ) Notice: Subject to any disclaimer, the term of this patent is extended or adjusted under 35 U.S.C. 154(b) by 536 days.

(21) Appl. No.: 15/052,770

(22) Filed: Feb. 24, 2016

(65) Prior Publication Data

US 2017/0112226 A1    Apr. 27, 2017

Related U.S. Application Data

(60) Provisional application No. 62/244,979, filed on Oct. 2, 2015.

(51) Int. Cl.
*A61F 9/06* (2006.01)

(52) U.S. Cl.
CPC .................... *A61F 9/064* (2013.01)

(58) Field of Classification Search
CPC ..... A61F 9/06; A61F 9/064; A41D 2600/202; A42B 3/228
USPC ................................ 2/8.2, 8.5, 8.6
See application file for complete search history.

(56) References Cited

U.S. PATENT DOCUMENTS

| | | | |
|---|---|---|---|
| 3,214,768 A | 11/1965 | Bohner | |
| 5,822,126 A * | 10/1998 | Cursolle | A42B 3/042 |
| | | | 359/630 |
| 5,829,103 A | 11/1998 | Allen | |
| 5,867,874 A | 2/1999 | Simpson | |
| 6,481,059 B2 | 11/2002 | Morris | |
| 8,505,121 B2 | 8/2013 | Ahlgren et al. | |
| 8,745,770 B2 | 6/2014 | Ahlgren et al. | |
| 9,066,552 B2 | 6/2015 | Ahlgren et al. | |
| 9,956,118 B2 * | 5/2018 | Sernfalt | A61F 9/06 |

(Continued)

FOREIGN PATENT DOCUMENTS

| | | |
|---|---|---|
| CN | 101827538 B | 9/2010 |
| EP | 2207443 A1 | 7/2010 |

OTHER PUBLICATIONS

Extended European Search Report for European Patent Application 14194740.8-1705 (dated Jul. 16, 2015).

*Primary Examiner* — Timothy K Trieu
(74) *Attorney, Agent, or Firm* — McClure, Qualey & Rodack, LLP

(57) ABSTRACT

Helmet assemblies with flip-type welding visors are provided. A representative helmet assembly includes: a grinding shell having a grinding view port; a welding visor mounted to the grinding shell and having a welding view port; and a connector extending between the grinding shell and the welding visor. The welding visor is rotatable between lower and upper positions. In the lower position, the welding view port is aligned with the grinding view port. In the upper position, the welding visor is rotated toward the back of the grinding shell such that the line of sight of the wearer is unobstructed by the welding view port. Interaction of the grinding shell, the connector and the welding visor, responsive to rotation of the welding visor between the lower and upper positions, provides a biasing force to urge the welding visor towards a selected one of the positions.

16 Claims, 8 Drawing Sheets

(56) References Cited

U.S. PATENT DOCUMENTS

| | | | |
|---|---|---|---|
| 2004/0179149 A1* | 9/2004 | Wang-Lee | A61F 9/061 349/58 |
| 2005/0108857 A1 | 5/2005 | Wartian et al. | |
| 2014/0298557 A1* | 10/2014 | Townsend, Jr. | A61F 9/06 2/8.2 |
| 2015/0250251 A1 | 9/2015 | Ahlgren et al. | |

* cited by examiner

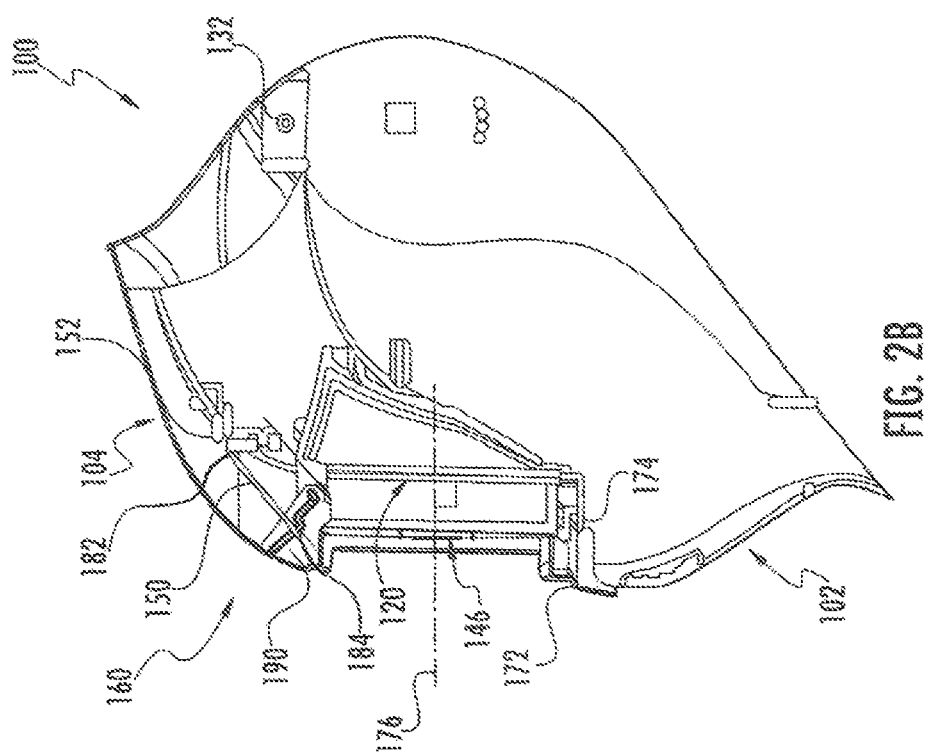
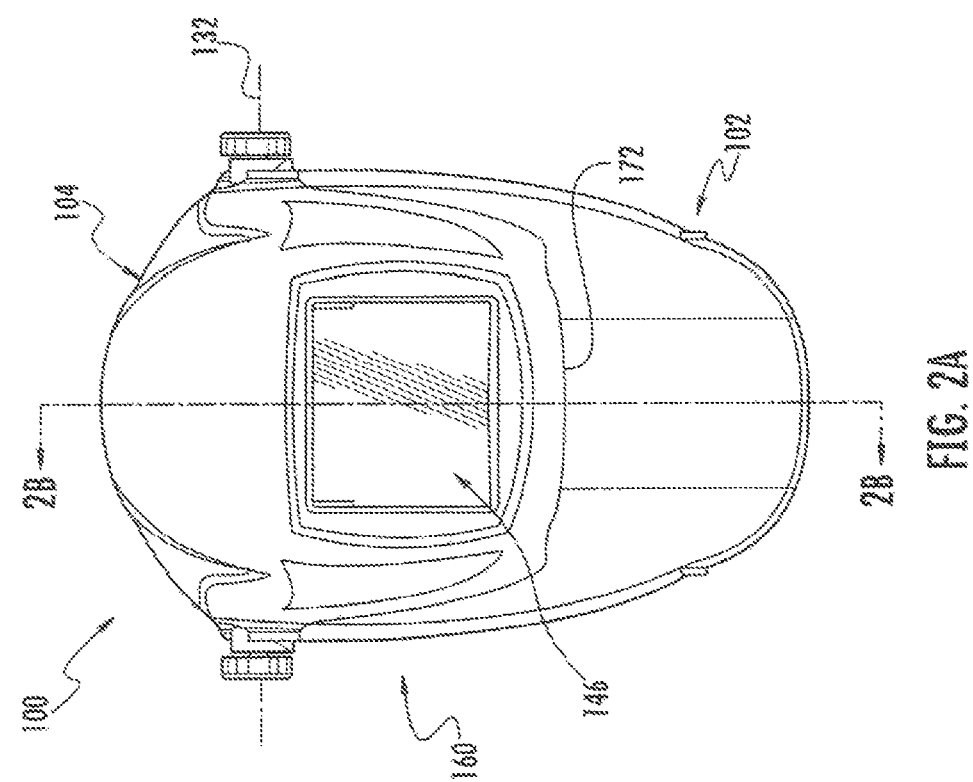

HELMET ASSEMBLIES WITH FLIP-TYPE WELDING VISORS

CROSS-REFERENCE TO RELATED APPLICATION

This utility application claims the benefit of and priority to U.S. Provisional Application 62/244,979, filed on Oct. 2, 2015, the disclosure of which is incorporated by reference herein in its entirety.

TECHNICAL FIELD

The present disclosure generally relates to welding helmets.

DESCRIPTION OF THE RELATED ART

Multi-purpose industrial helmets are known that provide numerous functional and safety features to a wearer. One such helmet is a flip-type helmet that incorporates head gear for mounting the helmet to the wearer and a movable welding visor. The welding visor may be moved or "flipped" down in front of the eyes of the wearer or flipped up away from the wearer's face. Unfortunately, retaining the welding visor in a desired position is not readily accomplished as the welding visors typically are rather heavy. Additionally, the helmets are often oriented in various positions that place heavy stresses on the associated mechanisms for retaining the selected positions of the welding visors.

SUMMARY

Helmet assemblies with flip-type welding visors are provided. Briefly described, one embodiment, among others, comprises: a grinding shell having a front, a back, an opening located at the back configured to receive the head of a wearer of the helmet assembly, and a grinding view port located at the front; a welding visor mounted to the grinding shell and having a welding view port, the welding visor being rotatable about a first rotational axis between a lower position and an upper position; and a connector extending between the grinding shell and the welding visor; in the lower position, the welding view port being aligned with the grinding view port such that a line of sight of the wearer of the helmet assembly extends through the grinding view port and the welding view port, and in the upper position, the welding visor being rotated toward the opening at the back of the grinding shell such that the line of sight of the wearer is unobstructed by the welding view port; wherein interaction of the grinding shell, the connector and the welding visor, responsive to rotation of the welding visor between the lower and upper positions, provides a biasing force to urge the welding visor towards a selected one of the positions.

Another embodiment comprises: a grinding shell having a front, a back, an opening located at the back configured to receive the head of a wearer of the helmet assembly, and a grinding view port located at the front; a welding visor mounted to the grinding shell and having a welding view port, the welding visor being rotatable about a first rotational axis between a lower position and an upper position; and a connector extending between the grinding shell and the welding visor; in the lower position, the welding view port being aligned with the grinding view port, and in the upper position, the welding visor being rotated toward the opening at the back of the grinding shell; wherein interaction of the grinding shell, the connector and the welding visor, responsive to rotation of the welding visor from the lower position to the upper position provides a biasing force to urge the welding visor towards the upper position, and responsive to rotation of the welding visor from the upper position to the lower position provides a biasing force to urge the welding visor towards the lower position.

Other systems, methods, features, and/or advantages of the present disclosure will be or may become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 2A is a front schematic view of an example embodiment of a helmet assembly, with the welding visor in the lower position.

FIG. 2B is a cross-sectional view of the embodiment of FIG. 2A as viewed along section line 2B-2B.

DETAILED DESCRIPTION

Figure 1:
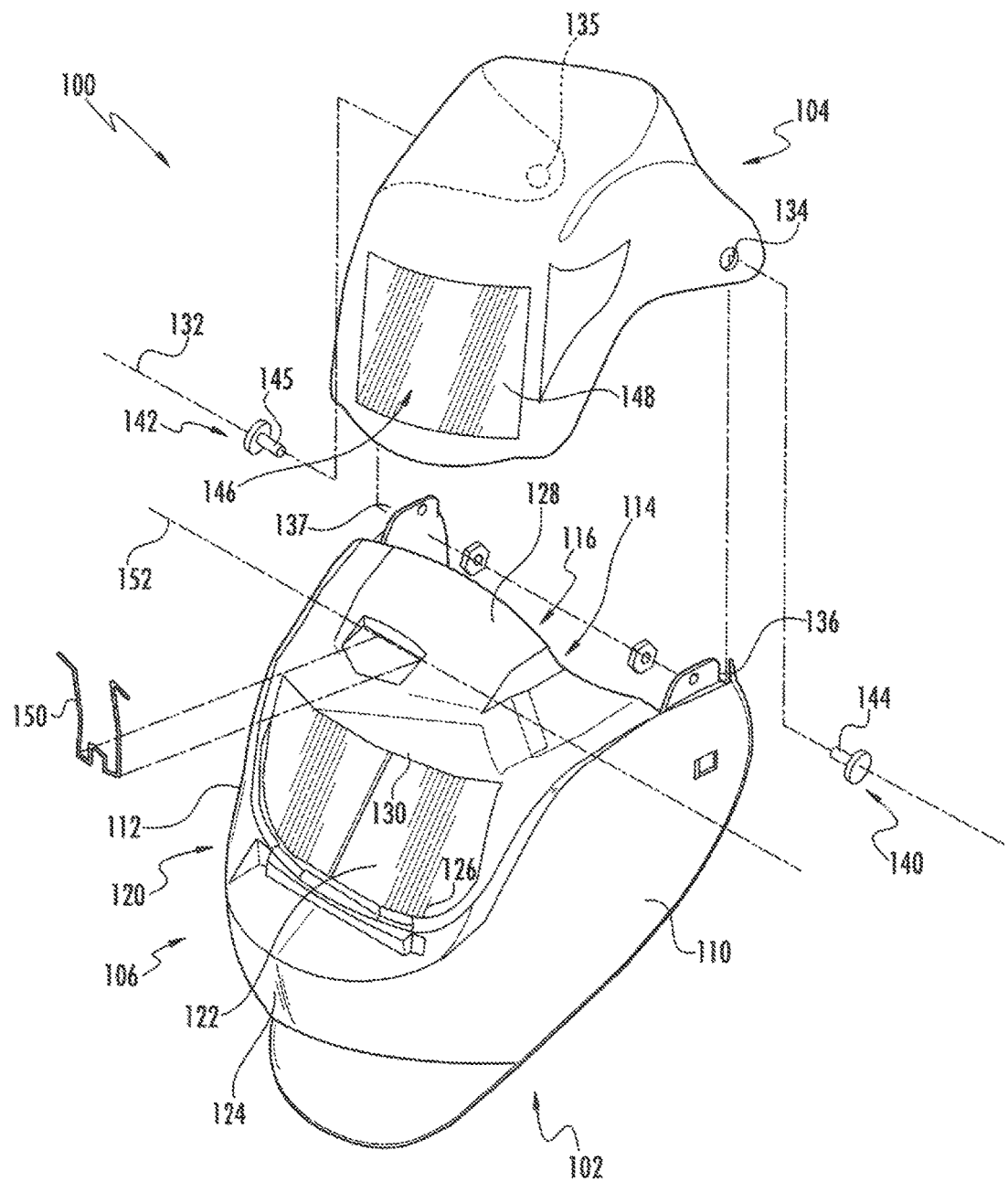
FIG. 1 is a schematic, exploded view of an example embodiment of a helmet assembly.

Having summarized various aspects of the present disclosure, reference will now be made in detail to that which is illustrated in the drawings. While the disclosure will be described in connection with these drawings, there is no intent to limit the scope of legal protection to the embodiment or embodiments disclosed herein. Rather, the intent is to cover all alternatives, modifications and equivalents included within the spirit and scope of the disclosure as defined by the appended claims.

In this regard, FIG. 1 is a schematic, exploded view of an example embodiment of a helmet assembly. As shown in FIG. 1, helmet assembly 100 includes a grinding shell 102 and a welding visor 104. The grinding shell 102 is configured to receive the head of a wearer, with mounting of the assembly to the wearer's head typically being accomplished by head gear (e.g., straps and/or bands) that is not shown in these figures. The grinding shell 102 has a front 106 for positioning near the face of a wearer, a left side 110 for positioning near the left cheek of the wearer, a right side 112 for positioning near the right cheek of the wearer, and a back 114. An opening 116 is located at the back 114 and is configured to receive the head of the wearer of the helmet assembly.

A grinding view port 120 is located at the front 106 that mounts a grinding cover plate 122 through which a wearer's line of sight is directed during a grinding operation, for example. Grinding view port 120 is defined, at least in part, by a chin portion 124 that spans between the left and right sides 110, 112 along a lower edge 126, and by a cranium portion 128 that spans between the left and right sides 110, 112 along an upper edge 130.

Welding visor 104 is mounted to grinding shell 102 and is rotatable about a rotational axis 132. In the embodiment depicted in FIG. 1, mounting of welding visor 104 to grinding shell 102 is facilitated by corresponding pairs of mounting apertures 134, 135 of welding visor 104 that align with apertures 136, 137 of grinding shell 102. Knob assemblies 140, 142 include shafts 144, 145 that extend through the apertures for retaining alignment of the apertures. In some embodiments, knob assemblies 140, 142 may enhance retention of welding visor 104 at selected positions about axis 132 by providing user-adjustable frictional engagement between welding visor 104 and grinding shell 102 such as by via an interposed rubber bushing (not shown).

Welding visor 104 incorporates a welding view port 146 that mounts a welding cover plate 148 through which a wearer's line of sight extends during a welding operation, for example. As will be described in greater detail, welding visor 104 is rotatable about rotational axis 132 between a lower position (depicted in FIG. 2A) and an upper position (depicted in FIG. 4A). In the lower position, welding visor 104 is seated against grinding shell 102 to prevent unwanted light leakage between the components. Additionally, welding view port 146 is aligned with grinding view port 120 so that a line of sight of the wearer of helmet assembly 100 extends through the grinding view port and then the welding view port. In the upper position, welding visor 104 is rotated toward the back 148 of the grinding shell so that the line of sight of the wearer is unobstructed by the welding visor. For instance, in this embodiment, the welding view port 146 is positioned above the cranium portion 128. It should be noted that the "line of sight" is a sight line extending through the grinding cover plate 122.

Also depicted in FIG. 1 is a connector 150 that extends between grinding shell 102 and welding visor 104. In this embodiment, connector 150 is a wireform that is rotatable about axis 152, which is parallel to but displaced from axis 132. Functionality of the connector will be described in detail later.

In operation, interaction of grinding shell 102 and welding visor 104 provides a biasing force to urge the welding visor towards a selected position (e.g., the lower position or the upper position). For instance, as the welding visor approaches the lower position, a biasing force is present that urges the welding visor downwardly against the grinding shell. The extent of the biasing force is derived from numerous factors, such as (but not limited to): contact surface shapes of the exterior of grinding shell 102 and the interior of welding visor 104; size and/or shape of the connector 150; location of the rotational axes (132, 152); attachment locations of the connector; and resilience of the materials forming grinding shell 102, welding visor 104 and connector 150. Preferably, the biasing force exhibited at the lower and upper positions is greater (e.g., minimally greater) than the weight of the welding visor (and any components installed thereon) in order to retain the desired position regardless of the orientation of the helmet assembly.

FIGS. 2A and 2B depict helmet assembly 100 with welding visor 102 in the lower position 160. As may be see more clearly in FIG. 2B, the lower position 160 is exhibited by lower edge 172 of welding visor 104 abutting ledge 174 of grinding shell 102 after the welding visor is rotated downwardly towards the grinding shell about axis 132. Welding visor 104 is retained in this position by a biasing force. In the lower position, line of sight 176 of a wearer of the helmet assembly extends through grinding view port 120 and welding view port 146. Preferably, welding view port 146 is aligned (to the extent possible) with grinding view port 120.

Connector 150, which extends between the exterior of grinding shell 102 and the interior of welding visor 104, includes a shell end 182 and a visor end 184. Shell end 182 is rotatably connected to grinding shell 102 so that the connector may rotate about axis 152. Visor end 184 of the connector engages welding visor 104 and assists in guiding the welding visor between the various positions relative to the grinding shell and/or to enhance the extent of biasing force applied to the welding visor. In this embodiment, engagement of connector 150 with welding visor 104 is facilitated by a pair of cam slots, only one of which (i.e., cam slot 190) is depicted in FIG. 2B. Specifically, visor end 184 of the connector engages and is guided by cam slot 190.

Figure 3B:
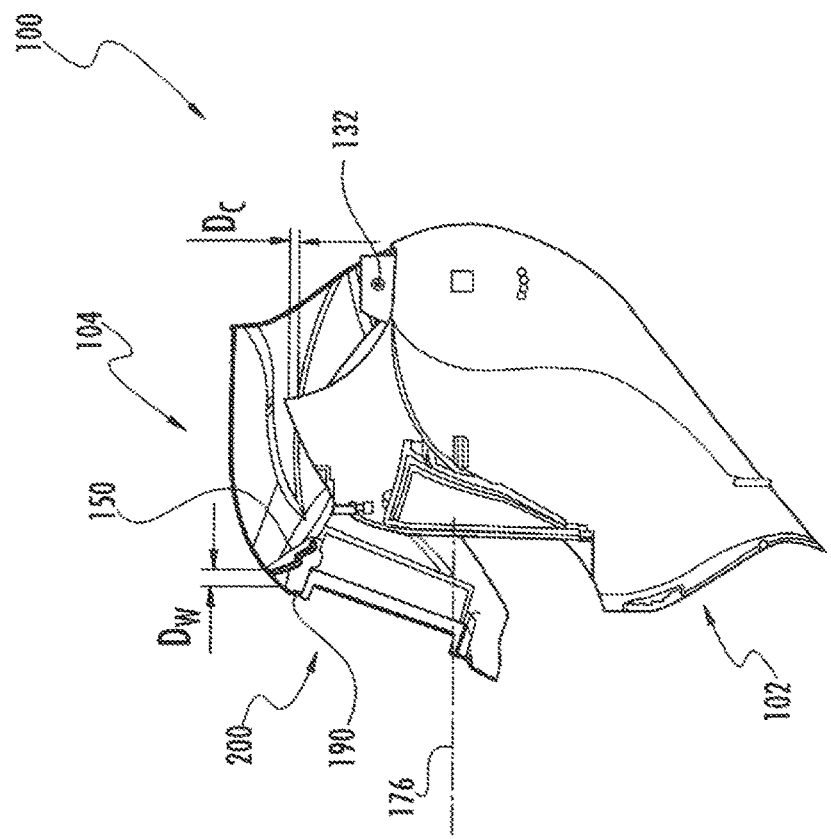
FIG. 3B is a cross-sectional view of the embodiment of FIG. 3A as viewed along section line 3B-3B.
Figure 3A:
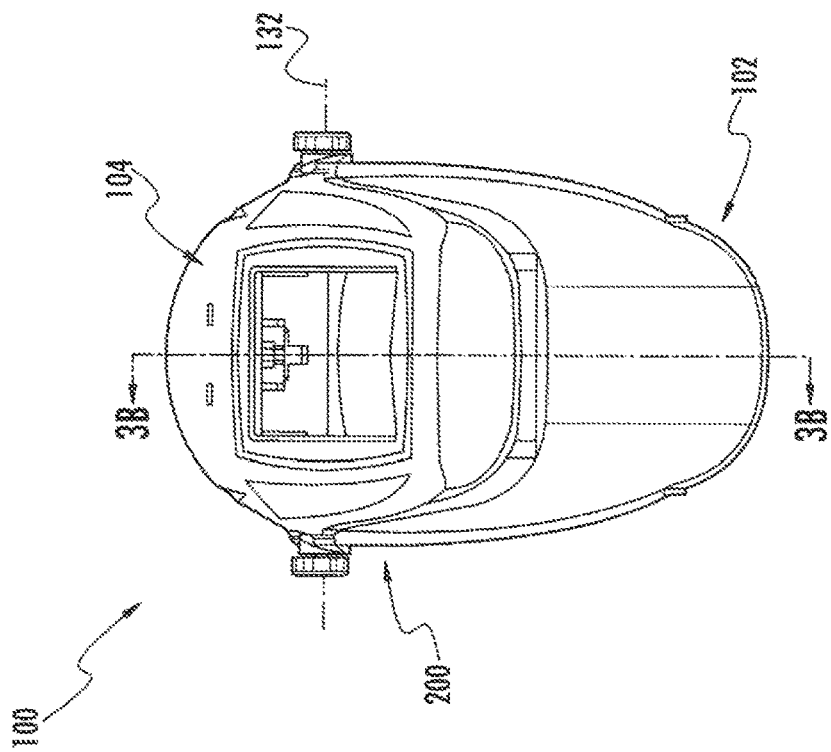
FIG. 3A is a front schematic view of the embodiment of FIGS. 2A and 2B, with the welding visor in the intermediate position.

FIGS. 3A and 3B depict the helmet assembly 100 with welding visor 104 in an intermediate position 200. As shown in FIG. 3B, the intermediate position 200 is exhibited by lower edge 172 of welding visor 104 at least partially obstructing the line of sight 176. Notably, welding visor 104 has been rotated upwardly and rearwardly toward the back 114 of the grinding shell about axis 132.

At intermediate position 200, the biasing force exerted upon welding visor 104 reaches a maximum as potential energy is loaded into various components of the helmet assembly. In this embodiment, deflection in the material of cranium portion 128 and connector 150 are evident (shown by arrows $D_C$ for the cranium portion and $D_W$ for the connector). Note that connector 150 is depicted for clarity at its non-deformed length (which does not actually occur in this embodiment), with arrows $D_W$ representing the difference in radial path of connector visor end 184 and the welding visor 104, which is later described more fully with respect to FIG. 9.

Figure 4B:
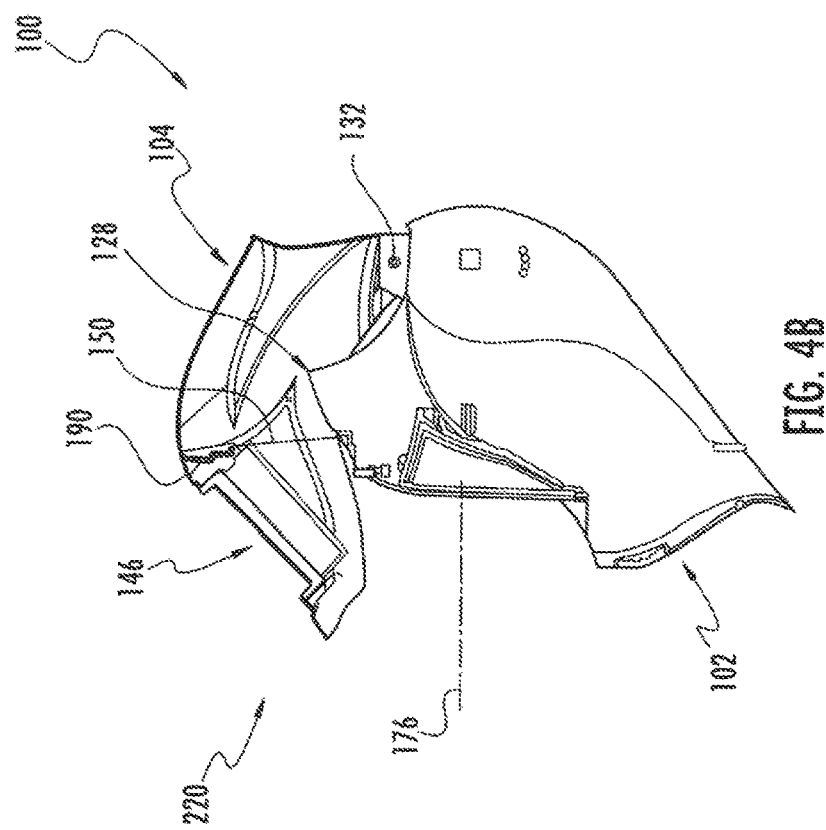
FIG. 4B is a cross-sectional view of the embodiment of FIG. 4A as viewed along section line 4B-4B.
Figure 4A:
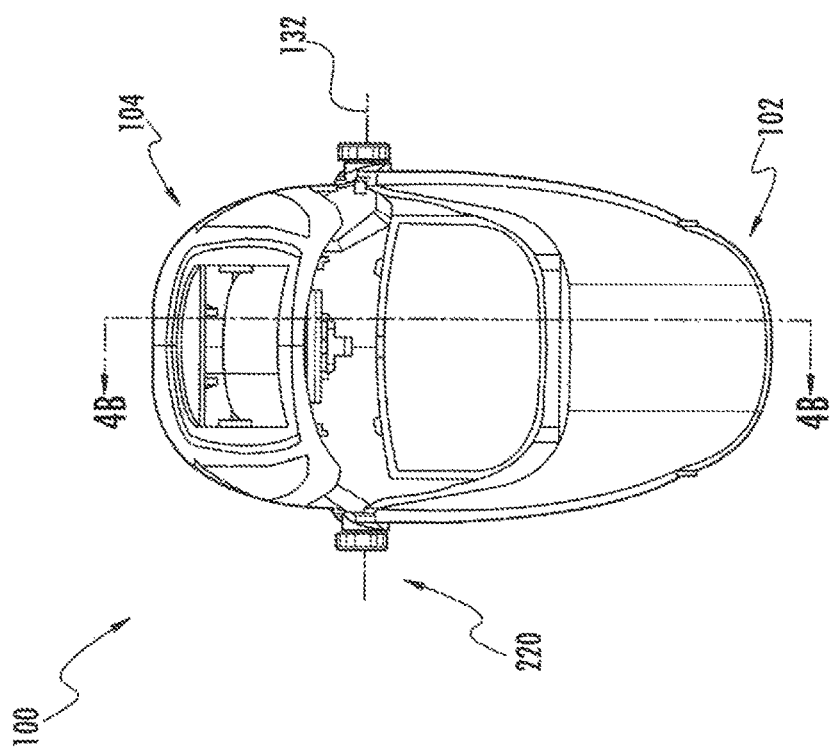
FIG. 4A is a front schematic view of the embodiment of FIGS. 2A-3B, with the welding visor in the upper position.

FIGS. 4A and 4B depict helmet assembly 100 with welding visor 104 in the upper position 220. As shown in FIG. 4B, the intermediate position 220 is exhibited by the line of sight 176 of the wearer being unobstructed by the welding visor 104. Notably, welding visor 104 has been rotated upwardly and rearwardly from the intermediate position toward the back 114 of the grinding shell about axis 132.

Figure 5:
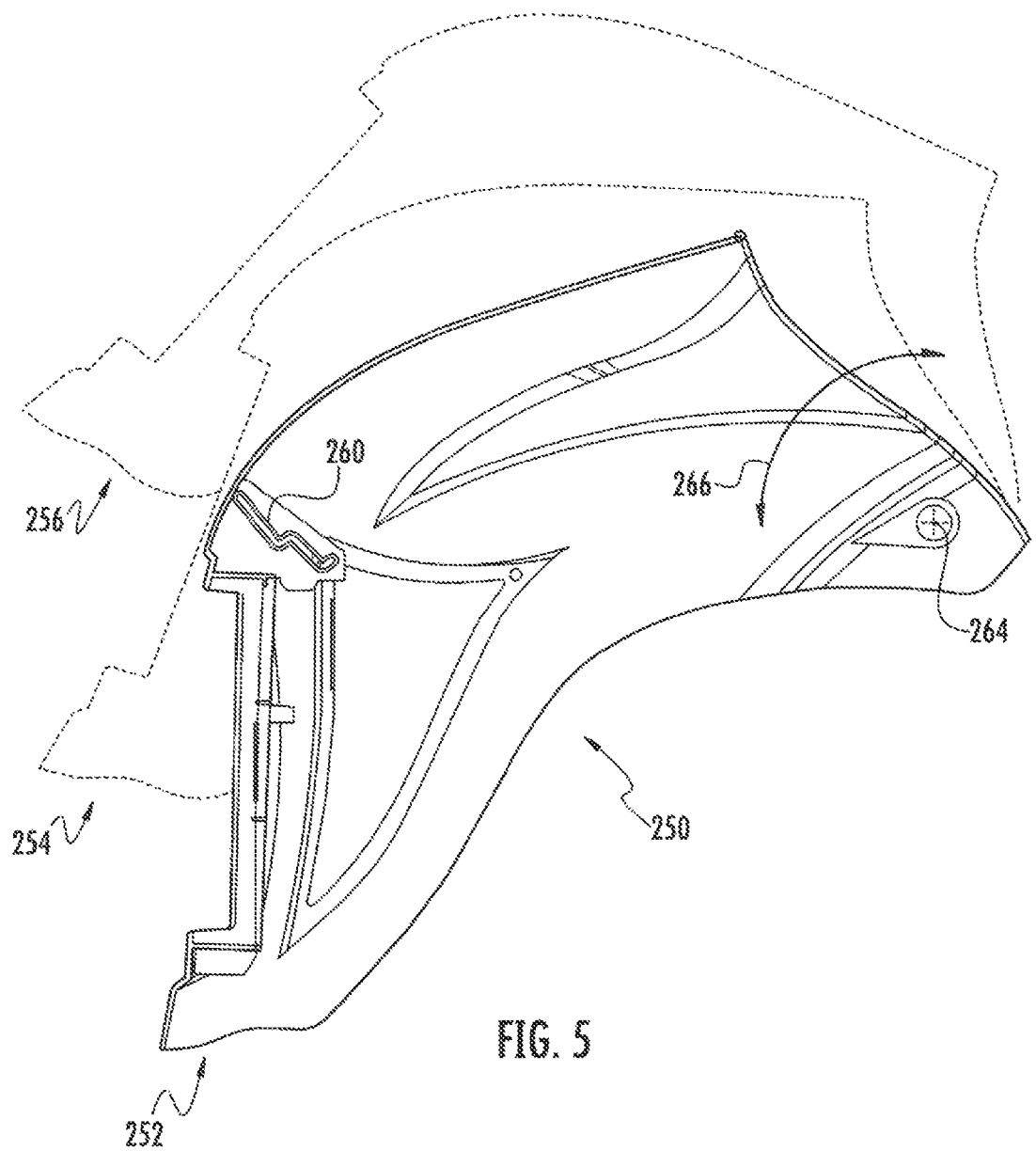
FIG. 5 is a schematic view of an example embodiment of a welding visor being rotated from the lower position, through the intermediate position, to the upper position, with the intermediate and upper positions being depicted in phantom lines.
Figure 6:
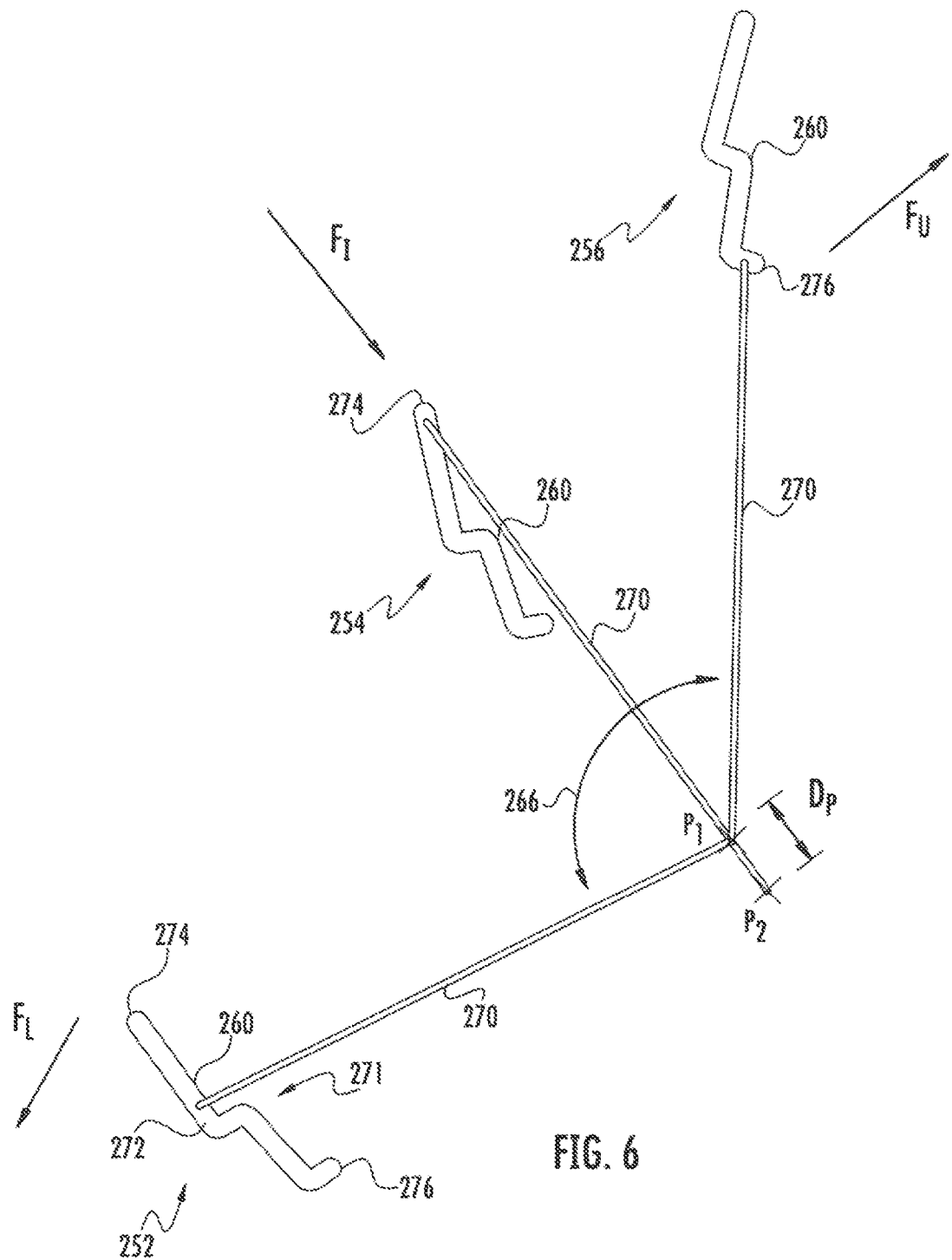
FIG. 6 is a schematic view of an example embodiment of a cam slot of the welding visor of FIG. 5 showing interaction of the cam slot and the connector.

FIGS. 5 and 6 depict a welding visor 250 being rotated from its lower position 252, through an intermediate position 254, to an upper position 256. In FIG. 5, the intermediate position 254 and upper position 256 of the welding visor are presented in phantom lines. Relative orientations of a representative cam slot 260, which is carried by an interior surface of the welding visor, are depicted with each location of the cam slot in FIG. 6 corresponding to a position of the welding visor shown in FIG. 5.

As shown in FIG. 5, repositioning of welding visor 250 from the lower position 252 to upper position 256 involves rotating the welding visor about axis 264 so that the welding visor moves through arc 266. As shown in FIG. 6, repositioning of welding visor 250 also involves the reorientation of cam slot 260 and interaction of the cam slot with connector 270.

In particular, at lower position 252, a biasing force (represented by vector $F_L$) is present for retaining the welding visor in the lower position. In this position, connector 270 extends from point of rotation ($P_1$) to an intermediate portion 271 of cam slot 260. As welding visor 250 is rotated along arc 266 toward intermediate position 254, distal end 272 of connector 270 is guided outwardly along the cam slot until seating at the radially outward end 274 of the cam slot.

Further movement of the welding visor along the arc with the connector seated at end 274 of the cam slot (i.e., the head of the cam slot) causes loading of the helmet assembly with potential energy resulting in deflection of the connector, welding visor and/or grinding shell. Note that during this movement, the biasing force has changed in direction and magnitude (represented by vector $F_I$). In this embodiment, the various deformations cause the repositioning of the point of rotation from $P_1$ to $P_2$ (the deflection of the point of rotation is expressed as $D_P$).

From intermediate position 254, continued movement of the welding visor along the arc 266 results in an unloading at least some of the potential energy as the point of rotation repositions to $P_1$. Further movement of the welding visor causes the distal end 272 of the connector to be guided to the radially inward end 276 of the cam slot (i.e., the foot of the cam slot). During this movement from position 254 to position 256, the biasing force has changed again in direction and magnitude (represented by vector $F_U$).

Figure 7:
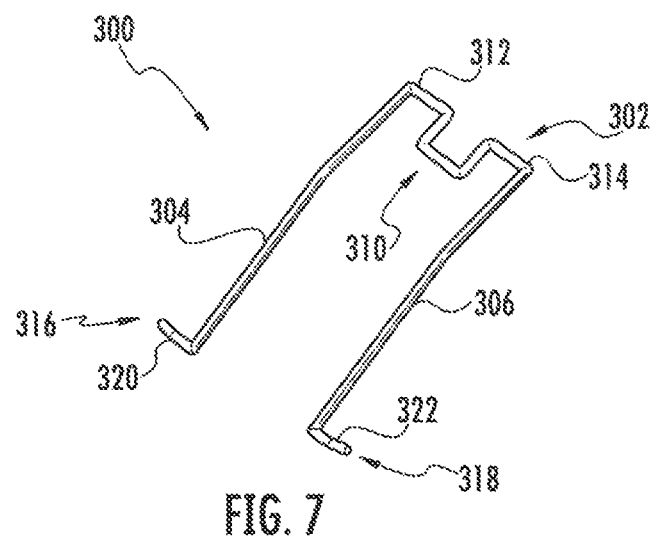
FIG. 7 is a schematic view of an example embodiment of a connector.

FIG. 7 depicts an example embodiment of a connector 300 configured as a wireform. As shown in FIG. 7, connector 300 is generally U-shaped incorporating a base 302 with arms 304, 306 extending outwardly therefrom. In this embodiment, base 302 includes an optional offset segment 310 located approximately midway between the ends 312, 314 of the base. The offset may be used to restrict side-to-side movement of the connector when implemented in conjunction with a corresponding stop positioned between the legs of the offset segment.

In the embodiment of FIG. 7, each of the arms 304, 306 exhibits an included angle of between approximately 150-170 degrees. Distal ends 316, 318 of the arms terminate in outwardly extending cams 320, 322 that are configured to engage within corresponding cam slots.

Figure 8:
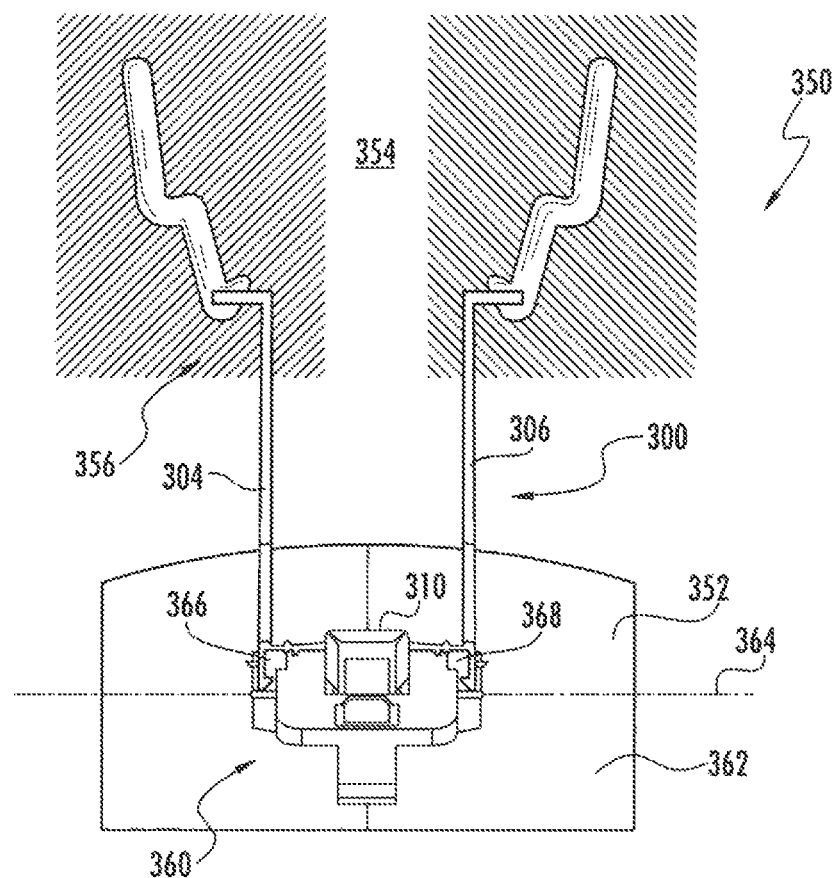
FIG. 8 is a schematic view of the connector of FIG. 7 shown retained in the upper position by an embodiment of a locking mechanism.

FIG. 8 depicts a helmet assembly 350 that includes a grinding shell 352, a welding visor 354 and connector 300 of FIG. 7. As shown in FIG. 8, the welding visor 354 is retained in the upper position 356 by an embodiment of a locking mechanism 360. Locking mechanism 360 assists in retaining welding visor 354 in the upper position by forming an interference fit with the arms 304, 306 of the connector. In particular, locking mechanism 360 is attached to cranium portion 362 of grinding shell 352 and serves as a mount for the base 302 of the connector. So attached, the connector is able to rotate about an axis 364 defined by the locking mechanism.

In one embodiment, locking lugs 366, 368 extend outwardly from locking mechanism 360. The locking lugs are positioned to capture arms 304, 306 of the connector by interference fit as the connector is carried by the welding visor during movement towards the upper position. As the arms encounter the locking lugs during this movement, continued application of force by the arms against the locking lugs deflects the arms outwardly from each other until the arms clear the locking lugs. Thus, the locking lugs form a mechanical lock of the welding visor when in the upper position that supplements the biasing force in retaining the position of the welding visor.

In another embodiment, the locking mechanism excludes locking lugs. In such an embodiment, locking of the welding visor in the upper position may be facilitated by the angles and shaped surfaces of the radially inward end 276 of the cam slot.

In order to disengage the mechanical lock, the welding visor 354 is urged toward the intermediate position with sufficient force to cause the arms to deflect away from each other for clearing the locking lugs of the locking mechanism.

Figure 9:
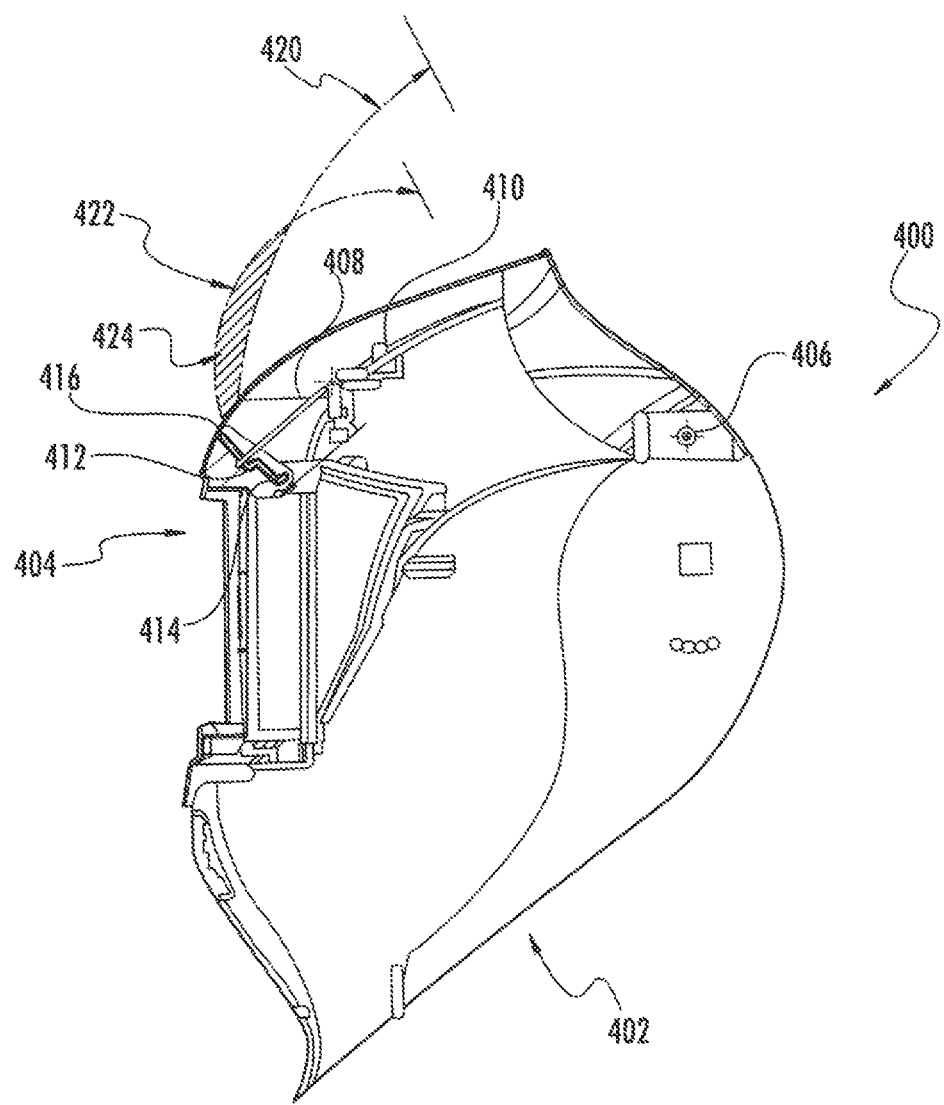
FIG. 9 is a cross-sectional view of an example embodiment of a helmet assembly.

FIG. 9 is a cross-sectional view of another embodiment of a helmet assembly 400, which includes a grinding shell 402 and a welding visor 404. Welding visor 404 is mounted to grinding shell 402 and is rotatable about a rotational axis 406. A connector 408 extends between grinding shell 402 and welding visor 404, with the connector being rotatable about axis 410. As in previous embodiments, distal ends of the connector (e.g., distal end 412 is shown in FIG. 9) ride in corresponding cam slots (e.g., slot 414).

As shown in FIG. 9, rotation of welding visor 404 about axis 406 results in the head 416 of cam slot 414 rotating along an arc 420 (depicted in dashed lines). Additionally, arc 422 (also depicted in dashed lines) represents the path along which the distal end 412 of connector 408 rotates when not being deflected during carriage by the welding visor—deflection typically occurs when connector 408 is attached to welding visor 404 resulting in biasing forces. Note that shaded region 424, which corresponds to the overlap of arcs 420 and 422, represents the locations and corresponding magnitude of biasing forces present within the helmet assembly during operation. These biasing forces are present because the distal ends of connector 408 are prevented from extending outwardly beyond the heads of the cam slot (which corresponds to arc 420) in which it rides, resulting in deflection of the connector and possibly one or more other components of the helmet assembly. These biasing forces urge the welding visor towards the selected position.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

At least the following is claimed:

1. A helmet assembly comprising:
    a grinding shell having a front, a back, an opening located at the back configured to receive the head of a wearer of the helmet assembly, and a grinding view port located at the front; a welding visor mounted to the grinding shell and having a welding view port, the welding visor being rotatable about a first rotational axis between a lower position and an upper position, in the lower position, the welding view port being aligned with the grinding view port such that a line of sight of the wearer of the helmet assembly extends through the grinding view port and the welding view port, and in the upper position, the welding visor being rotated toward the opening at the back of the grinding shell such that the line of sight of the wearer is unobstructed by the welding view port;

and a connector extending between the grinding shell and the welding visor;

wherein, responsive to rotation of the welding visor between the lower and upper positions, at least one of the grinding shell, the connector and the welding visor is configured to deflect, causing the connector to rotate about a second rotational axis displaced from the first rotational axis, resulting in a biasing force that is adapted to urge the welding visor towards a selected one of the positions.

2. The helmet assembly of claim 1, wherein: the welding visor exhibits an intermediate position located between the lower position and the upper position; and the biasing force increases as the welding visor is adapted to move by the user and approaches the intermediate position.

3. The helmet assembly of claim 1, wherein:
the connector extends between a shell end of the connector and a visor end of the connector, the shell end being rotatably connected to the grinding shell;
the welding visor has a cam slot; and
the visor end of the connector is guided by the cam slot.

4. The helmet assembly of claim 1, wherein:
the connector is U-shaped having a base with a first arm and a second arm extending outwardly from the base;
the base is rotatably connected to the grinding shell;
the welding visor has a first cam slot and a second cam slot; and
a distal end of the first arm is guided by the first cam slot and a distal end of the second arm is guided by the second cam slot.

5. The helmet assembly of claim 1, wherein:
the connector has a shell end and a visor end, the shell end being rotatably connected to the grinding shell;
the welding visor has a cam slot extending between a head and a foot thereof, the head being positioned radially outboard, with respect to an axis of rotation of the connector, from the foot;
the visor end of the connector is guided by the cam slot; and
the visor end of the connector is positioned at the head of the cam slot when the welding visor exhibits the intermediate position.

6. The helmet assembly of claim 5, wherein the visor end of the connector is positioned at the foot of the cam slot when the welding visor exhibits the upper position.

7. The helmet assembly of claim 5, wherein the visor end of the connector is positioned between the foot and the head of the cam slot when the welding visor exhibits the lower position.

8. The helmet assembly of claim 1, wherein the connector is a resilient wireform.

9. The helmet assembly of claim 1, wherein:
the helmet assembly further comprises a locking mechanism operative to retain the welding visor in the upper position by forming an interference fit with the connector;
the locking mechanism is configured such that moving of the welding visor from the upper position towards the intermediate position is adapted by the user disengages the interference fit by deflecting the first arm and the second arm of the connector away from each other to clear corresponding locking surfaces of the locking mechanism.

10. A helmet assembly comprising:
a grinding shell having a front, a back, an opening located at the back configured to receive the head of a wearer of the helmet assembly, and a grinding view port located at the front; a welding visor mounted to the grinding shell and having a welding view port, the welding visor being rotatable about a first rotational axis between a lower position and an upper position, in the lower position, the welding view port being aligned with the grinding view port, and in the upper position, the welding visor being rotated toward the opening at the back of the grinding shell; and
a connector extending between the grinding shell and the welding visor;
wherein, responsive to rotation of the welding visor between the lower and upper positions of the grinding shell, the connector and the welding visor responsive to rotation of the welding visor is adapted by a user from the lower position to the upper position provides a biasing force corresponding to material deflection of the grinding shell and the connector to urge the welding visor towards the upper position, and responsive to rotation of the welding visor is adapted by the user from the upper position to the lower position provides a biasing force corresponding to the material deflection of the grinding shell and the connector to urge the welding visor towards the lower position wherein the connector is rotatable about a second axis displaced from the first rotational axis.

11. The helmet assembly of claim 10, wherein the connector is a wireform connector.

12. The helmet assembly of claim 11, wherein:
the connector extends between a shell end and a visor end, the shell end being rotatably connected to the grinding shell;
the welding visor has a cam slot; and
the visor end of the connector is guided by the cam slot.

13. The helmet assembly of claim 11, wherein:
the connector has a shell end and a visor end, the shell end being rotatably connected to the grinding shell;
the welding visor has a cam slot with a head and a foot and extending therebetween, the head being positioned radially outboard, with respect to an axis of rotation of the connector, from the foot;
the visor end of the connector is guided by the cam slot; and
the visor end of the connector is positioned at the head of the cam slot when the welding visor exhibits the intermediate position.

14. The helmet assembly of claim 13, wherein the visor end of the connector is positioned at the foot of the cam slot when the welding visor exhibits the upper position.

15. The helmet assembly of claim 13, wherein the visor end of the connector is positioned between the foot and the head of the cam slot when the welding visor exhibits the lower position.

16. The helmet assembly of claim 10, wherein:
the helmet assembly further comprises a locking mechanism operative to retain the welding visor in the upper position by forming an interference fit with the connector;
the locking mechanism is configured such that moving of the welding visor from the upper position towards the intermediate position is adapted by the user disengages the interference fit by deflecting the first arm and the second arm of the connector away from each other to clear corresponding locking surfaces of the locking mechanism.

* * * * *